(12) United States Patent
Dong

(10) Patent No.: US 11,596,576 B2
(45) Date of Patent: Mar. 7, 2023

(54) ACUPUNCTURE ROBOT AND INTELLIGENT ACUPUNCTURE SYSTEM AND METHOD

(71) Applicant: Xibi Dong, Yichang (CN)

(72) Inventor: Xibi Dong, Yichang (CN)

(*) Notice: Subject to any disclaimer, the term of this patent is extended or adjusted under 35 U.S.C. 154(b) by 1026 days.

(21) Appl. No.: 16/328,552

(22) PCT Filed: May 10, 2017

(86) PCT No.: PCT/CN2017/083677
§ 371 (c)(1),
(2) Date: Feb. 26, 2019

(87) PCT Pub. No.: WO2018/133254
PCT Pub. Date: Jul. 26, 2018

(65) Prior Publication Data
US 2021/0308008 A1 Oct. 7, 2021

(30) Foreign Application Priority Data
Jan. 23, 2017 (CN) .......................... 201710051113.8

(51) Int. Cl.
*A61H 39/00* (2006.01)
*G06K 9/00* (2022.01)
(Continued)

(52) U.S. Cl.
CPC ....... *A61H 39/002* (2013.01); *A61N 1/36031* (2017.08); *G06T 7/74* (2017.01);
(Continued)

(58) Field of Classification Search
CPC .......... A61H 39/002; A61H 2201/1638; A61H 2201/1659; A61H 2201/501;
(Continued)

(56) References Cited

U.S. PATENT DOCUMENTS

2003/0191506 A1* 10/2003 Shloznikov ........ A61N 1/36021
607/46
2004/0220644 A1* 11/2004 Shalev ............... A61N 1/36082
607/45
(Continued)

FOREIGN PATENT DOCUMENTS

CN          1775170 A     5/2006
CN        101579553 A    11/2009
(Continued)

OTHER PUBLICATIONS

CN 101579553 A with English Translation (Year: 2009).*
(Continued)

*Primary Examiner* — Quang D Thanh
(74) *Attorney, Agent, or Firm* — Mai D. Lauer; Westman, Champlin & Koehler P.A.

(57) ABSTRACT

An acupuncture robot and an intelligent acupuncture system and method are provided. The acupuncture robot includes an acupuncture treatment host, a treatment electrode and a palm fixing frame, wherein the palm fixing frame is used for fixing a palm, and the treatment electrode is used for carrying out acupuncture massage treatment on holographic acupuncture points of a second metacarpal bone of the palm of a patient; and the acupuncture treatment host is in communication connection with a server to acquire an operation instruction, instructs, according to the operation instruction, the patient to use the acupuncture robot, and controls, according to the operation instruction, the treatment electrode such that same carries out acupuncture massage treatment on the holographic acupuncture points of the second metacarpal bone of the patient. The intelligent acupuncture system includes the acupuncture robot and the server.

15 Claims, 5 Drawing Sheets

(51) Int. Cl.
  *G06K 9/46* (2006.01)
  *G06T 7/73* (2017.01)
  *A61N 1/36* (2006.01)
  *G06V 10/44* (2022.01)
  *G06V 40/10* (2022.01)

(52) U.S. Cl.
  CPC .......... *G06V 10/44* (2022.01); *G06V 40/107* (2022.01); *A61H 2201/1638* (2013.01); *A61H 2201/1659* (2013.01); *A61H 2201/501* (2013.01); *A61H 2205/065* (2013.01); *G06T 2207/30196* (2013.01)

(58) Field of Classification Search
  CPC .......... A61H 2205/065; A61N 1/36031; A61N 1/0456; A61N 1/0502; A61N 1/0452; A61N 1/36017; G06T 7/74; G06T 2207/30196; G06V 10/44; G06V 40/107
  See application file for complete search history.

(56) References Cited

U.S. PATENT DOCUMENTS

| | | | |
|---|---|---|---|
| 2006/0074337 | A1 | 4/2006 | Yoo |
| 2013/0261493 | A1* | 10/2013 | Lin ............ A61B 5/0532 600/548 |
| 2014/0336492 | A1* | 11/2014 | Lin ............ A61B 5/0022 607/60 |
| 2016/0256103 | A1 | 9/2016 | Chang et al. |

FOREIGN PATENT DOCUMENTS

| | | |
|---|---|---|
| CN | 102743282 A | 10/2012 |
| CN | 103170058 A | 6/2013 |
| CN | 103479510 A | 1/2014 |

OTHER PUBLICATIONS

CN 103170058 A with English Translation (Year: 2013).*
First Office Action of corresponding Chinese patent application No. 201710051113.8, dated Dec. 12, 2018.
English translation of the first Office Action of corresponding Chinese patent application No. 201710051113.8, dated Dec. 12, 2018.
International Search Report of corresponding PCT application No. PCT/CN2017/083677, dated Sep. 6, 2017.
English translation of the International Search Report of corresponding PCT application No. PCT/CN2017/083677, dated Sep. 6, 2017.
English translation of abstract of Chinese patent application No. CN101579553A.
English translation of abstract of Chinese patent application No. CN102743282A.
English translation of abstract of Chinese patent application No. CN103170058A.
English translation of abstract of Chinese patent application No. CN103479510A.
Office Action for European Patent Appl. No. 17 893 356.0-1124, dated Dec. 17, 2019, 7 pages.

* cited by examiner

US 11,596,576 B2

ACUPUNCTURE ROBOT AND INTELLIGENT ACUPUNCTURE SYSTEM AND METHOD

CROSS-REFERENCE TO RELATED APPLICATIONS

This application is a Section 371 National Stage Application of International Application No. PCT/CN2017/083677, filed May 10, 2017 and published as WO/2018/133254 A1 on Jul. 26, 2018, which claims priority to Chinese Patent Application No. 201710051113.8, filed with the Chinese Patent Office on Jan. 23, 2017, entitled "Acupuncture Robot and Intelligent Acupuncture System", the contents of which are incorporated herein by reference in their entirety.

TECHNICAL FIELD

The present disclosure relates to the field of medical healthcare devices, and in particular to an acupuncture robot and an intelligent acupuncture system and method.

BACKGROUND ART

Electroacupuncture massage treatment (or therapy) is one of the healthcare and treatment methods commonly used at this stage. At present, the commonly used electroacupuncture massage treatment modes mainly include the following two modes:

The first type is the hand-held treatment pen method, wherein the treatment is performed by aligning a hand-held treatment pen with an acupoint (or acupuncture point) of a human body by a doctor, and only one acupoint can be treated at each time. The disadvantage is that the palms of a patient cannot be fixed, and the doctor needs to hold the hand-held treatment pen for a long time, which leads to the tiredness of hands.

The second type is the palm binding method, that is to say, an electrode is bound to a palm using a binding strap, the doctor aligns the electrode with an acupoint of a patient and presses the electrode against the acupoint and then binds the electrode onto the patient's palm, and an electrical pulse generator (a host of the therapeutic apparatus) is energized to treat the patient with electrical pulses. This is the earliest mode implemented in electrical pulse therapeutic apparatuses, i.e. fixing an electrode to a palm, and its disadvantage is that it is difficult to accurately locate an acupoint, the acupoint is pressed at poor accuracy, the fixation is inconvenient, and it is difficult for a patient to achieve both a tight binding with the palm and an accurate alignment with the acupoint, which brings a bottleneck for the popularization of electrical pulse treatments.

SUMMARY

In view of this, an object of the present disclosure is to provide an acupuncture robot to improve the above-mentioned problems.

Another object of the present disclosure is to provide an intelligent acupuncture system to improve the above-mentioned problems.

Another object of the present disclosure is to provide an intelligent acupuncture method to improve the above-mentioned problems.

The present disclosure is implemented as follows:

In a first aspect, an embodiment of the present disclosure provides an acupuncture robot, the acupuncture robot comprises: an acupuncture treatment host, a palm fixing frame, and a treatment electrode, wherein the acupuncture treatment host is mounted to the palm fixing frame, and the treatment electrode is embedded in the palm fixing frame and electrically connected with the acupuncture treatment host; the acupuncture treatment host comprises a control unit, a communication unit, and an electrical pulse circuit, both the communication unit and the electrical pulse circuit are connected with the control unit, and the control unit is configured to receive and process data; the communication unit is configured to establish a communication connection between the control unit and a server so as to acquire an operation instruction sent by the server and send a therapeutic effect (treatment effect) to the server; the electrical pulse circuit is further connected with the treatment electrode and configured to output an electrical pulse signal to the treatment electrode according to the operation instruction under the control of the control unit to perform acupuncture massage treatment on a patient, and the palm fixing frame is configured to fix a palm of the patient; and the treatment electrode is configured to convert the electrical pulse signal into electrical stimulation to perform acupuncture massage treatment on the patient.

Further, the communication unit is specifically configured to acquire the operation instruction from the server according to an instruction from the control unit, wherein the operation instruction comprises acupoints for acupuncture treatment of the patient, the time (duration) of the acupuncture treatment of the patient, the number of times of the acupuncture treatments of the patient, and a current magnitude for the acupuncture treatment of the patient.

Further, the palm fixing frame comprises a grip rod and a treatment baseplate; wherein the grip rod comprises a grip portion and a movable portion, the movable portion comprises a first connecting portion and a second connecting portion opposite to the first connecting portion, the first connecting portion of the movable portion is rotatably connected with the treatment baseplate, and the grip portion is rotatably connected with the second connecting portion.

Further, the treatment baseplate comprises a control plate and a treatment plate, the acupuncture treatment host is mounted to the control plate, and the treatment electrode is embedded in the treatment plate.

Further, the treatment electrode comprises a substrate, a first electrode, a plurality of second electrodes, and a housing, wherein the substrate is provided with a plurality of mounting portions, positions where the plurality of mounting portions are distributed on the substrate are matched with a distribution of acupoints of a preset prescriptive map of therapeutic acupoints, and each of the first electrode and the second electrodes is corresponding to and mounted to one of the mounting portions.

Further, the housing has a shape and size matching the substrate, the housing is provided with a plurality of through holes, a position of each of the through holes is corresponding to a position of a respective mounting portion, and the treatment electrode is exposed through the through holes.

Further, the treatment electrode further comprises an electronic tag, and the electronic tag is mounted to the substrate and configured to store disease information of the patient and physiological feature information of the patient.

Further, the acupuncture treatment host further comprises an identification unit, the identification unit is connected with the control unit, and the identification unit is configured to read the feature information stored in the electronic tag.

Further, each of the first electrode and the second electrodes comprises a metal member, a base, and an (electrically) conductive spring, wherein the metal member comprises a first end and a second end, the first end extends over the base and is fixedly connected with the base, the conductive spring is disposed at the first end, and the conductive spring is connected with an output terminal of the substrate.

Further, the acupuncture treatment host further comprises a button unit and a display unit, wherein the button unit and the display unit are electrically connected with the control unit, respectively, the button unit is configured to obtain an operation instruction inputted by a user, and the control unit is configured to process the operation instruction and transmit the operation instruction to the display unit for display.

Further, the acupuncture robot further comprises an image acquisition unit and a driving unit, wherein both the image acquisition unit and the driving unit are electrically connected with the control unit, the image acquisition unit is configured to acquire a palm image of a hand of a user and transmit the palm image to the control unit, and the control unit is configured to outline an outer contour line of the hand based on the palm image and determine a curve feature, judge whether a position of head acupoint in the palm image is consistent with a position of a red indicating line for head acupoint of a pre-stored acupoint image, and control the driving unit to drive the palm fixing frame to adjust an angle if the judgment result is "not consistent".

Further, the acupuncture robot further comprises an image acquisition unit and a speaker, wherein the image acquisition unit and the speaker are electrically connected with the control unit, respectively, the image acquisition unit is configured to acquire a palm image of a hand of a user and transmit the palm image to the control unit, and the control unit is configured to outline an outer contour line of the hand based on the palm image and determine a curve feature, judge whether a position of head acupoint in the palm image is consistent with a position of a red indicating line for head acupoint of a pre-stored acupoint image, and generate a voice prompt based on the judgment result, and transmit the voice prompt to the speaker for playing.

Further, the acupuncture treatment host further comprises a power source, wherein the power source is electrically connected with the control unit, the communication unit, and the electrical pulse circuit, respectively, and configured to supply power to the control unit, the communication unit, the electrical pulse circuit, and the treatment electrode.

Further, the power source comprises a storage battery, an overvoltage and overcurrent protection circuit, and a voltage stabilizing circuit, wherein the storage battery, the overvoltage and overcurrent protection circuit, the voltage stabilizing circuit, and the control unit are electrically connected sequentially.

Further, the communication unit is a wireless communication unit, wherein the wireless communication unit comprises at least one of a GPRS module, a Bluetooth transmission module, an infrared transceiver module and a WIFI module.

In a second aspect, an embodiment of the present disclosure also provides an intelligent acupuncture system, comprising: a server and an acupuncture robot, the acupuncture robot comprising: an acupuncture treatment host, a palm fixing frame, and a treatment electrode, wherein the acupuncture treatment host is mounted to the palm fixing frame, and the treatment electrode is embedded in the palm fixing frame; the acupuncture treatment host comprises a control unit, a communication unit, and an electrical pulse circuit, the control unit, the electrical pulse circuit, and the treatment electrode are electrically connected sequentially, the communication unit is electrically connected with the control unit and configured to establish a communication connection with the server, and the control unit is configured to obtain a transmitted operation instruction and process the operation instruction; the electrical pulse circuit is configured to output an electrical pulse signal to the treatment electrode after receiving the processed operation instruction transmitted by the control unit, the treatment electrode is configured to convert the electrical pulse signal into electrical stimulation to perform acupuncture massage treatment on a patient, the acupuncture robot is in communication connection with the server, an operation instruction is stored in the server, and the acupuncture robot acquires the operation instruction from the server, and performs acupuncture massage treatment on the patient according to the operation instruction.

In a third aspect, an embodiment of the present disclosure also provides an intelligent acupuncture method applicable to the acupuncture robot described above, the intelligent acupuncture method comprising steps of:

receiving a palm image transmitted by an image acquisition unit;

outlining an outer contour line of a hand based on the palm image and determining a curve feature;

judging whether a position of head acupoint in the palm image is consistent with a position of a red indicating line for head acupoint of a pre-stored acupoint image; and controlling, if the judgment result is "not consistent", the driving unit to drive the palm fixing frame to adjust an angle until the position of the head acupoint in the palm image is consistent with the position of the red indicating line for head acupoint of the pre-stored acupoint image.

Compared with the prior art, the present disclosure has the following advantageous effects:

The present disclosure provides an acupuncture robot and an intelligent acupuncture system and method, comprising an acupuncture treatment host, a palm fixing frame, and a treatment electrode, wherein the treatment electrode is tailor-made (customized) for a patient, and stores physiological feature information and disease information of the patient; the palm fixing frame is capable of fixing a palm, such that a doctor does not need to hold a hand-held treatment pen for a long time to perform acupuncture treatment, thereby improving the doctor's operational experience of, and the palm fixing frame assists in the alignment of the treatment electrode with acupoints of the patient where acupuncture massage treatment is required, thereby improving the accuracy of accurately pressing the acupoints and facilitating the fixation, whereby both binding of the palm and alignment with the acupoints are satisfied, therefore the disclosure has the characteristic of a good prospect of popularization.

Additionally, the acupuncture treatment host is configured to be in communication connection with a server, and may send a therapeutic effect to the server and acquire an operation instruction from the server. The intelligent acupuncture system comprises an acupuncture robot and a server. The acupuncture robot acquires an operation instruction from the server and performs acupuncture massage on a patient according to the operation instruction, and may also send a therapeutic effect to the server. The invention of the acupuncture robot and the intelligent acupuncture system and method enables medical personnel to grasp the treatment condition of a patient in time, and to remotely instruct the patient to operate and use the acupuncture robot to provide better service to the patient.

In order to enable the above objects, features, and advantages of the present disclosure to be more apparent and easily understandable, preferred embodiments will be described below in detail by way of example and with reference to the accompanying drawings.

BRIEF DESCRIPTION OF DRAWINGS

In order to make the objects, technical solutions, and advantages of the embodiments of the present disclosure more clear, the technical solutions of the embodiments of the present disclosure will be described below clearly and completely with reference to the drawings of the embodiments of the present disclosure. It is apparent that the embodiments to be described are some, but not all of the embodiments of the present disclosure. Generally, the components of the embodiments of the present disclosure, as described and illustrated in the figures herein, may be arranged and designed in a wide variety of different configurations. Thus, the following detailed description of the embodiments of the present disclosure, as represented in the figures, is not intended to limit the scope of the present disclosure as claimed, but is merely representative of selected embodiments of the present disclosure. All the other embodiments obtained by those of ordinary skill in the art in light of the embodiments of the present disclosure without inventive efforts would fall within the scope of the present disclosure as claimed.

REFERENCE NUMERALS

Figure 1:
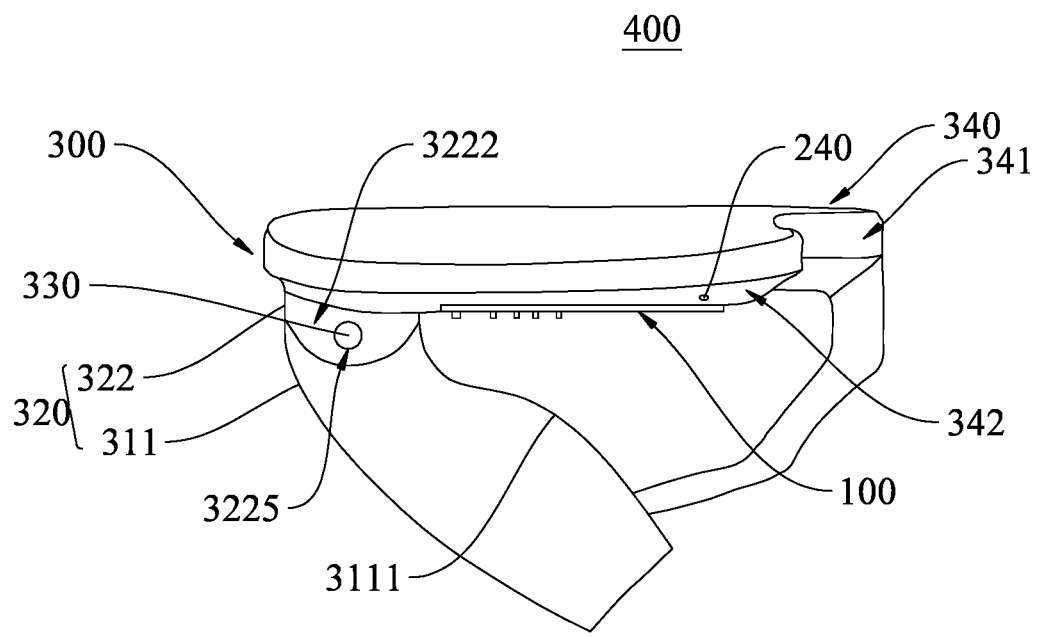
FIG. 1 shows a structural schematic diagram of an acupuncture robot according to the present disclosure.

100—treatment electrode; 110—substrate; 112—input terminal; 120—electrode; 121—metal member; 1211—first end; 1212—second end; 1213—conductive spring; 123—first electrode; 124—second electrode; 130—tag; 140—housing; 141—panel; 142—through hole; 143—side wall; 200—acupuncture treatment host; 210—control unit; 220—identification unit; 230—communication unit; 240—image acquisition unit; 250—speaker; 260—button unit; 270—display unit; 280—electrical pulse circuit; 290—power source; 291—overvoltage and overcurrent protection circuit; 292—voltage stabilizing circuit; 293—storage battery; 300—palm fixing frame; 320—grip rod; 311—grip portion; 3111—arcuate protrusion; 322—movable portion; 3222—second connecting portion; 3225—second hole; 330—rotating shaft; 340—treatment baseplate; 341—control plate; 342—treatment plate; 400—acupuncture robot; 500—server; 600—intelligent acupuncture system.

DETAILED DESCRIPTION OF EMBODIMENTS

The technical solutions of the embodiments of the present disclosure will be described below clearly and completely with reference to the drawings of the embodiments of the present disclosure. It is apparent that the embodiments to be described are some, but not all of the embodiments of the present disclosure. Generally, the components of the embodiments of the present disclosure, as described and illustrated in the figures herein, may be arranged and designed in a wide variety of different configurations. Thus, the following detailed description of the embodiments of the present disclosure, as represented in the figures, is not intended to limit the scope of the present disclosure as claimed, but is merely representative of selected embodiments of the present disclosure. All the other embodiments obtained by those skilled in the art in light of the embodiments of the present disclosure without inventive efforts would fall within the scope of the present disclosure as claimed.

It should be noted that similar reference numerals and letters refer to similar items in the following figures, and thus once an item is defined in one figure, it may not need to be further defined or explained in the following figures.

In the description of the present disclosure, it should be noted that orientation or positional relations indicated by the terms such as "up", "down", "left", "right", "inside", "outside", and the like are the orientation or positional relations shown based on the figures, or the orientation or positional relations in which the inventive product is conventionally placed in use, and these terms are intended only to facilitate the description of the present disclosure and simplify the description, but not intended to indicate or imply that the referred devices or elements must be in a particular orientation or constructed or operated in the particular orientation, and therefore should not be construed as limiting the present disclosure.

In the description of the present disclosure, it should also be noted that terms "disposed", "mounted", "coupled", and "connected" should be understood broadly unless otherwise expressly specified or defined. For example, connection may be fixed connection or detachable connection or integral connection, may be mechanical connection or electric connection, or may be direct coupling or indirect coupling via an intermediate medium or internal communication between two elements.

In the description of the present disclosure, it should also be noted that in this text, relational terms such as first, second, and the like are used only for distinguishing one entity or operation from another entity or operation, while it is not necessarily required or implied that these entities or operations have any such practical relation or order. The terms "horizontal", "vertical", "overhang", or the like do not mean that a component is required to be absolutely horizontal or overhanging, but means that the component may be slightly inclined. For example, the term "horizontal" simply means that its direction is more horizontal than that of the term "vertical", and does not mean that the structure must be completely horizontal, but means that the structure may be slightly inclined. The terms "comprise", "include", or any variations thereof are intended to cover non-exclusive inclusions, such that a process, method, article, or device that comprises a list of elements not only comprises those elements, but also comprises other elements not expressly listed or also comprises elements inherent to such process, method, article, or device. Without more restrictions, an element defined with the wording "comprising a . . . " does not exclude the presence of additional identical elements in the process, method, article, or device comprising said element. The specific meanings of the above-mentioned terms in the present disclosure could be understood by those of ordinary skill in the art according to specific situations.

Some embodiments of the present disclosure will be described in detail below with reference to the accompanying drawings. Embodiments described below and features in the embodiments may be combined with each other without conflict.

First Embodiment

Referring to FIG. 1, the present embodiment provides an acupuncture robot 400, wherein the acupuncture robot 400 comprises an acupuncture treatment host 200, a palm fixing frame 300, and a treatment electrode 100. Both the acupuncture treatment host 200 and the treatment electrode 100 are mounted to the palm fixing frame 300.

Figure 2:
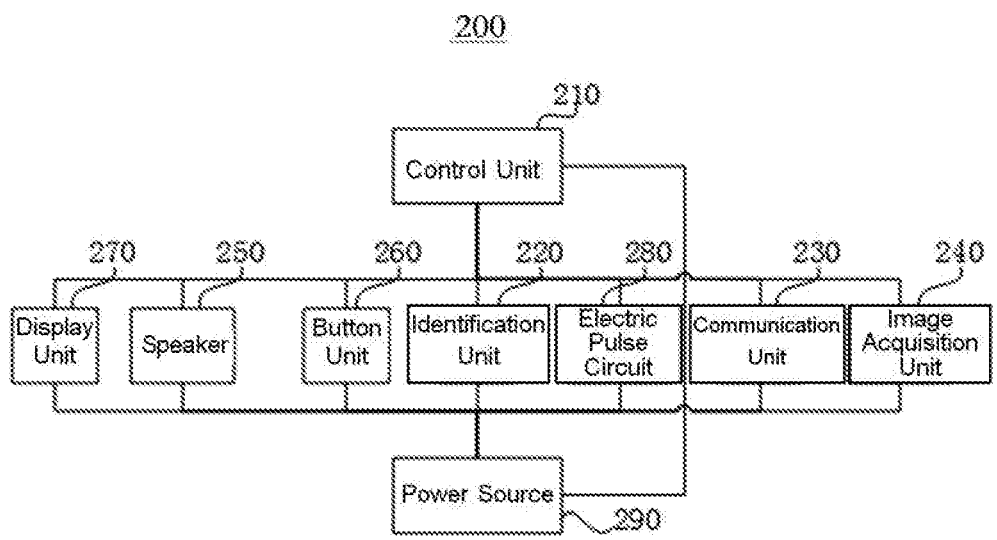
FIG. 2 shows a block diagram of circuit connection of an acupuncture treatment host according to the present disclosure.

Referring to FIG. 2, the acupuncture treatment host 200 comprises a control unit 210, an identification unit 220, a communication unit 230, an image acquisition unit 240, a speaker 250, a button unit 260, a display unit 270, and an electrical pulse circuit 280. The control unit 210 is electrically connected with each of the identification unit 220, the communication unit 230, the button unit 260, the display unit 270, and the electrical pulse circuit 280, the acupuncture treatment host 200 further comprises a power source 290, wherein the power source 290 is electrically connected with each of the control unit 210, the identification unit 220, the communication unit 230, the button unit 260, the display unit 270, and the electrical pulse circuit 280. Here, the control unit 210, the electrical pulse circuit 280, and the treatment electrode 100 are electrically connected sequentially.

The control unit 210 is a control center of the acupuncture treatment host 200, and controls the coordinated working and running of each element of each part of the acupuncture treatment host 200. In the present embodiment, the control unit 210 is selected from a single-chip microcomputer, but is not limited thereto, and may be other element having the same or similar functions such as a microcomputer in other embodiments. The control unit 210 is configured to obtain a transmitted operation instruction and process the operation instruction. Here, the control unit 210 may obtain an operation instruction by means of obtaining an operation instruction inputted by a user in the button unit 260, or by means of receiving, via the communication unit 230, an operation instruction transmitted by a server, which means is not limited herein.

The treatment electrode 100 comprises an electronic tag 130, the identification unit 220 is configured to identify feature information of the treatment electrode 100 stored in the electronic tag 130 of the treatment electrode 100, optionally, the feature information comprises physiological feature information (the name, gender, age, and length of a second metacarpal bone) and treatment information (disease information, an acupoint prescription for acupuncture treatment, the number of times of acupuncture treatments, the duration of acupuncture treatment, etc.) of a patient corresponding to the treatment electrode 100, and the identification unit 220 identifies the feature information and transfers the feature information to the control unit 210. In the present embodiment, the electronic tag 130 of the treatment electrode 100 may be a radio frequency identification (RFID) tag, and the identification unit 220 provided in the present embodiment may be employed as an RFID reader/writer, but is not limited thereto, and other devices satisfying the identification function are also possible. An RFID device is a non-contact device whose basic principle is to achieve automatic identification of an object to be identified by using transmission characteristics of radio frequency signals and spatial coupling (inductive or electromagnetic coupling) or radar reflection. The RFID reader/writer (RFID reader) wirelessly communicates with the RFID tag via an antenna, and can implement an operation of reading or writing an identification code and memory data of the RFID tag. A typical RFID reader/writer contains an RFID radio frequency module (transmitter and receiver), a controller, and a reader antenna. The spatial (contactless) coupling of a radio frequency signal is implemented between the RFID tag and the RFID reader/writer via a coupling element, and the transfer of the radio frequency signal and data exchange are implemented in a coupling channel according to the time sequence relations.

The communication unit 230 is electrically connected with the control unit 210, and is also in communication connection with a server 500 and configured to establish a communication between the acupuncture treatment host 200 and the server 500, and the communication unit 230 may receive an information sending instruction transmitted by the control unit 210, send feature information of the treatment electrode 100 identified by the identification unit 220 to the server 500, and receive an operation instruction sent by the server 500, wherein the operation instruction comprises acupoints for acupuncture massage treatment of a patient, the time (duration) of the acupuncture massage treatment of the patient, the number of times of the acupuncture massage treatments of the patient, a current magnitude for the acupuncture massage treatment of the patient, and so on. The communication unit 230 is further configured to acquire a preset image of acupoints of a patient from the server 500 after receiving an information acquisition instruction transmitted by the control unit 210, and send an effect of the acupuncture massage treatment to the server 500 after receiving an information sending instruction transmitted by the control unit 210, so as to instruct the patient to use the acupuncture robot 400 and intelligently organize and record the progress of the treatment of the patient, etc. In an embodiment of the present disclosure, the communication unit 230 is a wireless communication unit, and may be, for example, at least one of a GPRS module, a Bluetooth transmission module, an infrared transceiver module and a WIFI module.

The button unit 260 is electrically connected with the control unit 210 and configured to acquire an operation instruction from the user and establish an interaction between the acupuncture treatment host 200 and the user. In addition to acquisition of an operation instruction from the server, in the present embodiment, the control unit 210 may also acquire an operation instruction via the button unit 260. Specifically, in the present embodiment, the button unit 260 comprises a plurality of function buttons, including: a confirm button, a function confirmation button, a left selection button, a right selection button, and a quit button, and the button unit 260 may also be virtual buttons on a touch screen.

Figure 3:
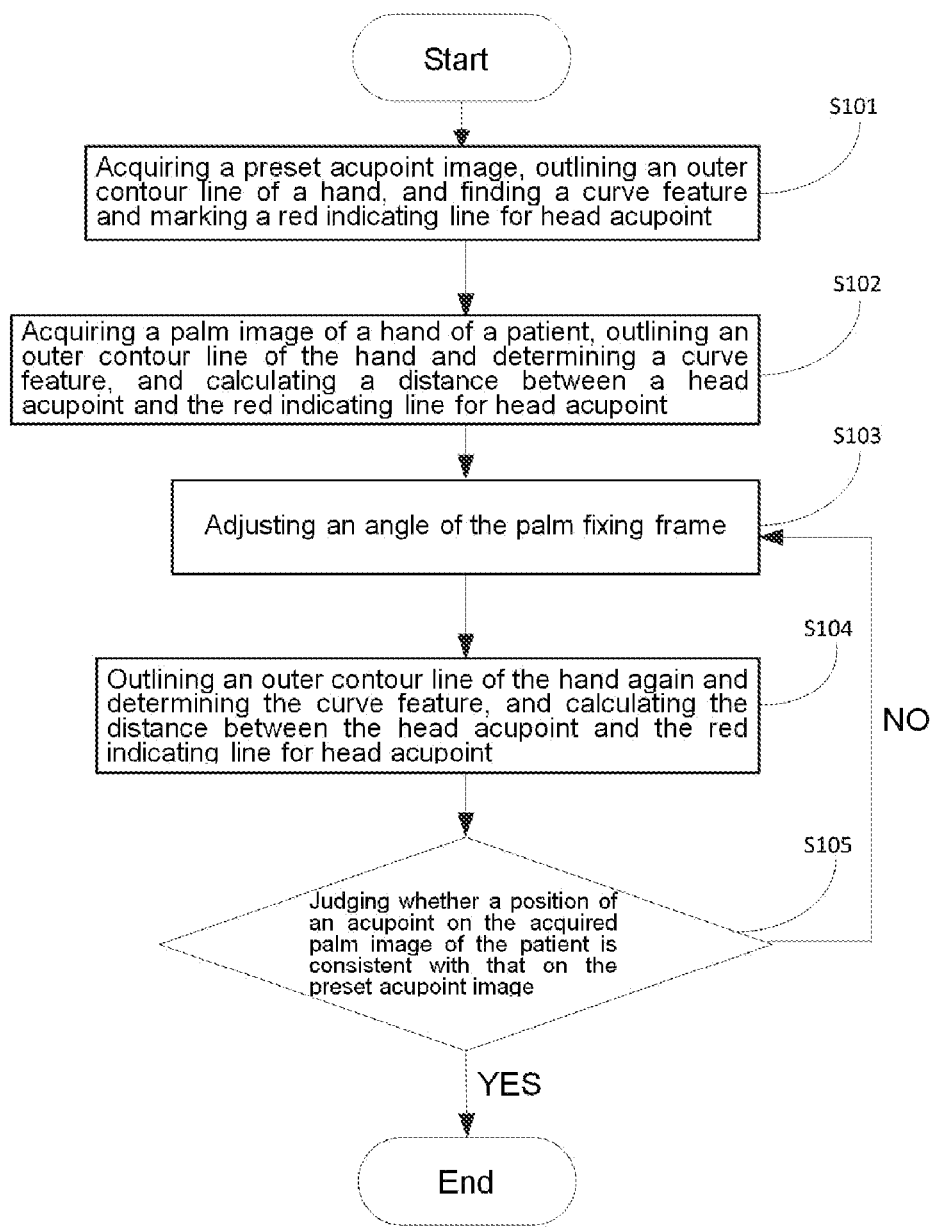
FIG. 3 shows a flowchart of adjusting a position of a palm to be aligned with an acupoint distribution of a preset acupoint image according to an embodiment of the present disclosure.

The acupuncture treatment host 200 further comprises an image acquisition unit 240 and a speaker 250, wherein the image acquisition unit 240 and the speaker 250 are electrically connected with the control unit 210, respectively, and the image acquisition unit 240 is configured to acquire a palm image when the patient uses the acupuncture robot 400, and send the palm image to the control unit 210. In the present embodiment, the image acquisition unit 240 is a camera, and according to a preset image processing algorithm, the control unit 210 prompts the patient via the display unit 270 and the speaker 250 to adjust a forward-backward position and an angle of a grip rod 320 of the palm fixing frame 300, so that the treatment electrode 100 is aligned with holographic acupoints of a second metacarpal bone of the patient. Referring to FIG. 3, the specific process of adjusting a position of a palm to be aligned with an acupoint distribution of a preset acupoint image is performed as follows:

Step S101: acquiring a preset acupoint image, outlining an outer contour line of a hand, finding a curve feature, and marking a red indicating line for head acupoint. This step is accomplished by the control unit 210 and the communication unit 230. The control unit 210 controls the communication unit 230 to acquire a preset acupoint image from the server 500, wherein the preset acupoint image comprises an outer contour line of a hand outlined in advance and a marked red indicating line for head acupoint.

Step S102: acquiring a palm image of a hand of a patient, outlining an outer contour line of the hand and determining a curve feature, and judging and calculating a distance between a head acupoint and the red indicating line for head acupoint. This step is accomplished by the control unit 210 and the image acquisition unit 240. The control unit 210 controls the image acquisition unit 240 to capture a palm image of a hand of a patient when the patient uses the acupuncture robot 400, outline an outer contour line of the hand according to a color difference between the palm and the background, and mark a red indicating line for head acupoint.

Step S103: adjusting an angle of the palm fixing frame 300.

Step S104: outlining again an outer contour line of the hand and determining again a curve feature, and calculating the distance between the head acupoint and the red indicating line for head acupoint.

The distance between the head acupoint and the red indicating line for head acupoint is analyzed by comparing a difference between the red indicating line for head acupoint marked in the image acquired by the image acquisition unit 240 and the red indicating line for head acupoint in the acquired preset acupoint image.

Step S105: judging whether an acupoint on the acquired palm image of the patient is consistent with the position of the acupoint on the preset acupoint image, and repeating the step S103 if the judgment result is "not consistent"; and ending the process if the judgment result is "consistent". The control unit 210 instructs the patient via the display unit 270 or the speaker 250 to adjust the angle of the grip rod 320 of the palm fixing frame 300 until the red indicating line for head acupoint in the acquired palm image coincides with the red indicating line for head acupoint in the acquired preset acupoint image.

By the above steps, the control unit 210 sends, via the display unit 270 or the speaker 250, a prompt such as moving the palm fixing frame 300, to instruct the patient to use the acupuncture robot 400, so that the treatment electrode 100 is aligned with acupoints of the patient where acupuncture massage treatment is required, with an error less than 0.1 mm.

In another more preferable manner, the acupuncture robot further comprises a driving unit, wherein the driving unit is electrically connected with the control unit 210, and the control unit 210 is configured to outline an outer contour line of the hand based on the palm image and determine a curve feature, judge whether the position of the head acupoint in the palm image is consistent with the position of the red indicating line for head acupoint of the pre-stored acupoint image, and control the driving unit to drive the palm fixing frame 300 to adjust the angle if the judgment result is "not consistent". In this way, an automatic alignment of the position of the head acupoint in the palm image with the position of the red indicating line for head acupoint of the pre-stored acupoint image can be achieved, and the doctor's operational experience of or patient is further improved.

Figure 4:
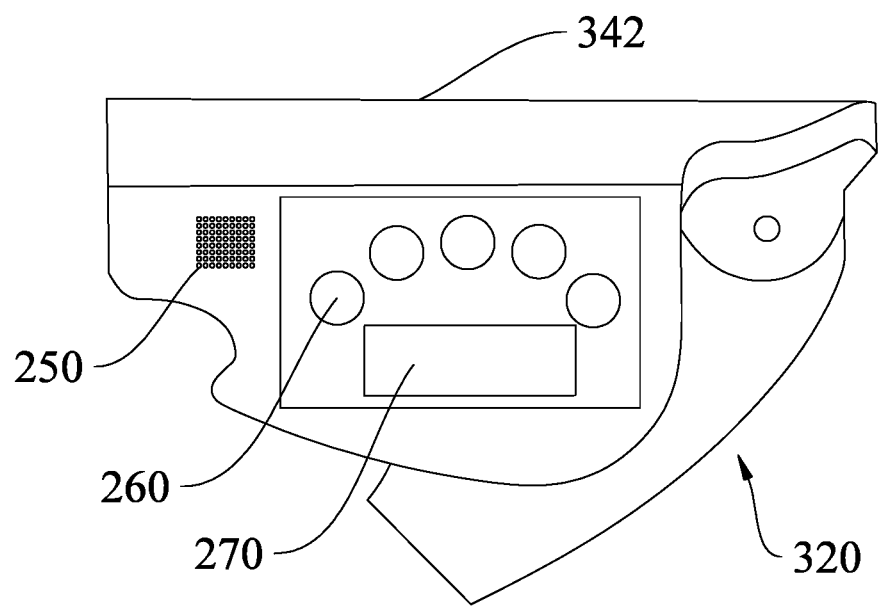
FIG. 4 shows a view of first angle of an acupuncture robot according to an embodiment of the present disclosure.

The display unit 270 is electrically connected with the control unit 210, and is configured to provide an interactive interface between the acupuncture treatment host 200 and the patient with reference to FIG. 4. The display unit 270 may display information such as the mode and time (duration) of acupuncture massage treatment, acupoints for the acupuncture massage treatment, demonstration of a usage method, etc. For example, when the patient is to be subjected to acupuncture massage treatment using the acupuncture robot 400, the acupuncture treatment host 200 instructs the patient to use the acupuncture robot 400, and usage steps may be displayed by the display unit 270 to instruct the patient to adjust the angle of the grip rod 320 of the palm fixing frame 300 so that the treatment electrode 100 is aligned with acupoints of the patient where the acupuncture massage treatment is required, and the patient is instructed to autonomously adjust the function and so on.

The power source 290 is electrically connected with each of the control unit 210, the identification unit 220, the communication unit 230, the button unit 260, the display unit 270, and the electrical pulse circuit 280, and is configured to supply power for normal working of the control unit 210, the identification unit 220, the communication unit 230, the button unit 260, the display unit 270, and the electrical pulse circuit 280. The power source 290 comprises a storage battery 293 or a rechargeable battery, and the storage battery 293 may be selected and used in the present embodiment. The palm fixing frame 300 comprises a grip rod 320, wherein the grip rod 320 is provided therein with a hollow cavity, and the storage battery 293 is disposed in the cavity and is connected with the control unit 210, the identification unit 220, the communication unit 230, the button unit 260, the display unit 270, the electrical pulse circuit 280, and so on via (conducting) wires.

Figure 5:
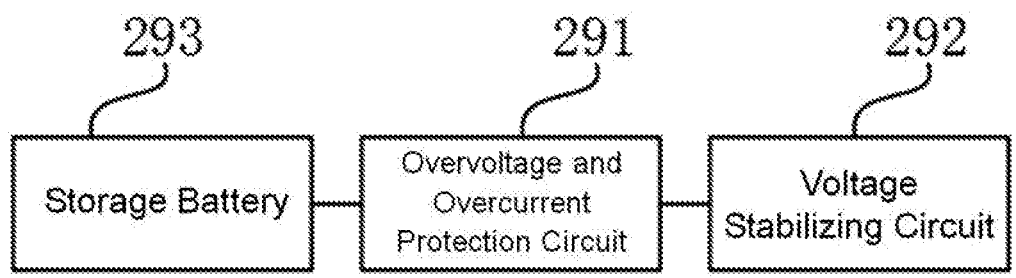
FIG. 5 shows a block diagram of circuit connection of a power source according to an embodiment of the present disclosure.

Referring to FIG. 5, the power source 290 further comprises an overvoltage and overcurrent protection circuit 291 and a voltage stabilizing circuit 292, wherein the storage battery 293, the overvoltage and overcurrent protection circuit 291, and the voltage stabilizing circuit 292 are electrically connected sequentially; when a voltage or current supplied by the power source 290 exceeds the rated working voltage or the rated working current of some components of the acupuncture treatment host 200, the overvoltage and overcurrent protection circuit 291 is automatically disconnected, which can prevent the components of the acupuncture treatment host 200 from being damaged. The voltage stabilizing circuit 292 can ensure that the power source 290 still outputs an electrical signal which is kept constant when the load, voltage, ambient temperature, circuit parameter or the like changes, avoiding an unstable electric energy supply from the power source 290.

The electrical pulse circuit 280 is electrically connected with the control unit 210 and the power source 290, respectively, and is also connected with the treatment electrode 100, wherein the electrical pulse circuit 280 comprises a pulse signal output terminal, and the pulse signal output terminal is electrically connected with an input terminal 112 of the treatment electrode 100 and configured to output an electrical pulse signal to the treatment electrode 100 under the control of the control unit 210. The treatment electrode 100 converts the electrical pulse signal into electrical stimulation to simulate the acupuncture massage treatment.

The palm fixing frame 300 comprises a treatment baseplate 340 and a grip rod 320, wherein the grip rod 320 further comprises a grip portion 311 and a movable portion 322. The grip rod 320 is movable forward and backward as well as leftward and rightward. The grip portion 311 is a rigid plastic rod, and an arcuate protrusion 3111 is disposed at an intermediate location of the grip portion 311, so that the palm of a hand is fitted to the arcuate protrusion 3111 when the arcuate protrusion 3111 is held in the hand, and so that the back of the hand and the thumb are in the form of holding an egg in the hand when the grip portion 311 is held in the hand. The movable portion 322 is a soft rubber column, and comprises a first connecting portion (not shown in figures) and a second connecting portion 3222 which are oppositely disposed, wherein the first connecting portion is rotatably connected with the treatment baseplate 340, and the second connecting portion 3222 is rotatably connected with the grip portion 311. Specifically, the second connecting portion 3222 is provided with a groove (not shown in figures), a first hole (not shown in figures) and a second hole 3225 coaxial with each other and having the same size are provided in the groove, one end of the grip portion 311 is provided with a third hole (not shown in figures), and a rotating shaft 330 sequentially passes through the first hole, the third hole, and the second hole 3225 so that the grip portion 311 is rotatable relative to the movable portion 322.

Figure 6:
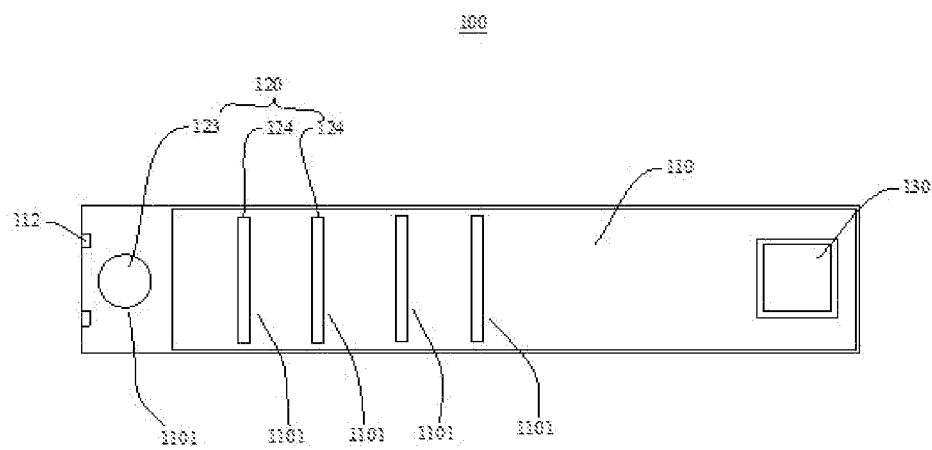
FIG. 6 shows a structural schematic diagram of a treatment electrode according to an embodiment of the present disclosure.

The treatment baseplate 340 comprises a control plate 341 and a treatment plate 342. Optionally, as shown in FIG. 6, the treatment electrode 100 comprises a first electrode 123 and a plurality of second electrodes 124, the control plate 341 and the treatment plate 342 are connected in an arcuate shape, and the curvature between the control plate 341 and the treatment plate 342 is comparable to the curvature between the back of the hand and the back of the thumb when an egg is held in the hand of a person. The treatment plate 342 is provided with a rectangular groove (not shown in figures) matching the treatment electrode 100, and the treatment electrode 100 is disposed in the rectangular groove and is electrically connected with the electrical pulse circuit 280 of the acupuncture treatment host 200 via a wire. When the hand of the patient holds the grip portion 311, an angle between the grip portion 311 and the movable portion 322 is adjusted such that the first electrode 123 of the treatment electrode 100 is aligned with the head acupoint of the second metacarpal bone of the patient, and at the same time the plurality of second electrodes 124 are aligned respectively with the remaining acupoints where acupuncture massage treatment is required, whereupon the acupuncture message treatment can be carried out.

The acupuncture treatment host 200 is mounted to the control plate 341 and configured to control the treatment electrode 100 to perform acupuncture massage treatment on the patient, the treatment electrode 100 is electrically connected with the electrical pulse circuit 280 by a wire to receive an electrical pulse signal, and the electrical pulse signal is converted by the treatment electrode 100 into electric stimulation to simulate the acupuncture massage treatment.

Figure 7:
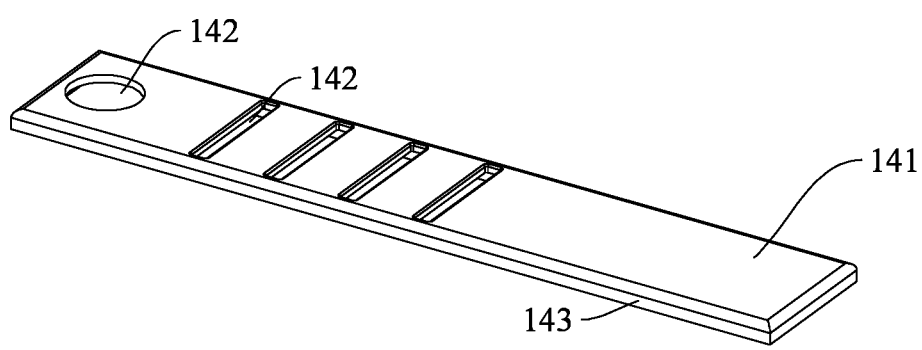
FIG. 7 shows a structural schematic diagram of a housing of treatment electrode according to an embodiment of the present disclosure.

Referring to FIG. 6 and FIG. 7, the treatment electrode 100 comprises a housing 140, a substrate 110, an electronic tag 130, and a plurality of electrodes 120, wherein the electronic tag 130 and each of the electrodes 120 are mounted to the substrate 110.

The electronic tag 130 is disposed on the substrate 110, and the electronic tag 130 stores feature information of the treatment electrode 100, the feature information of the treatment electrode 100 including: physiological feature information such as the name, age, gender, and length of a second metacarpal bone of a patient, and disease information of the patient. The feature information stored in the electronic tag 130 is the identity information of the treatment electrode 100. Since each patient has different physiological feature information and suffers from a different disease, each treatment electrode 100 corresponds to a different electronic tag 130, and the various treatment electrodes 100 are distinguished by the information within the electronic tags 130. In the present embodiment, a radio frequency identification (RFID) tag is preferably selected and used, and with the RFID, a specific target can be identified by means of a radio signal and related data can be read and written without establishing a mechanical or optical contact between the identification system and the specific target. In other embodiments of the present disclosure, other elements that can read and write information may also be selected and used as the electronic tag 130.

The substrate 110 is provided with a plurality of mounting portions (not shown in figures) according to a preset prescriptive map of therapeutic acupoints, each of the mounting portions may be a mounting hole or a welding point, and the preset prescriptive map of therapeutic acupoints is a map of acupoint prescriptions and locations for acupuncture treatment against the disease of the patient. For example, if the treatment against a disease of a patient requires acupuncture on acupoints such as head acupoint, shoulder-hand acupoint, and heart-lung acupoint, and the length of a second metacarpal bone of the patient is known, the mounting portions may be disposed on the substrate 110 according to the relative positions of the head acupoint, the shoulder-hand acupoint, the heart-lung acupoint and the like, and then the electrodes 120 are mounted to the mounting portions 1101 respectively, and for example, the electrodes 120 are welded to the mounting portions respectively. In the present embodiment, the substrate 110 may be a circuit board, but is not limited thereto, the circuit board comprises an input terminal 112 and a plurality of output terminals (not shown in figures), each of the output terminals is electrically connected with the input terminal 112, and each mounting portion corresponds to one output terminal; the input terminal 112 is connected with the electrical pulse circuit 280 of the acupuncture treatment host 200 for receiving an electrical pulse signal outputted by the electrical pulse circuit 280, each of the output terminals is further connected with the respective electrode 120 for conducting the electrical pulse signal to the electrode 120, and the electrical pulse signal is converted into electrical stimulation by the electrodes 120 to perform acupuncture massage treatment on the patient.

Figure 8:
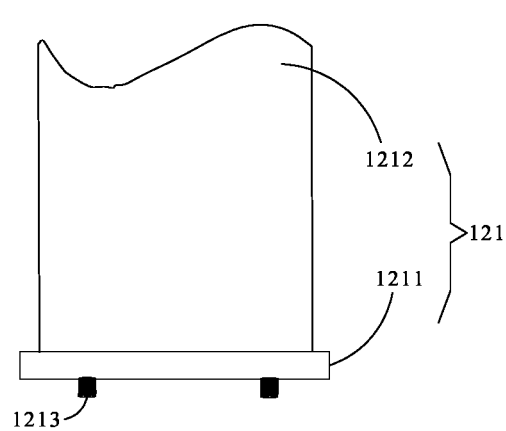
FIG. 8 shows a structural schematic diagram of an electrode according to an embodiment of the present disclosure.

Referring to FIG. 8, each of the electrodes 120 comprises a metal member 121 and a base, wherein the metal member 121 comprises a first end 1211 and a second end 1212, the first end 1211 extends over the base and is fixedly connected with the base, and specifically, the base is provided with a plurality of soldering legs which may be welded to the welding points provided at the respective mounting portion; the first end 1211 is further provided with conductive springs 1213, each conductive spring 1213 is connected with a respective output terminal of the substrate 110, and for example, the conductive spring 1213 may be welded to the respective output terminal of the substrate 110. In the present embodiment, the electrodes 120 are divided into a first electrode 123 and second electrodes 124; wherein the first electrode 123 is configured to perform acupuncture on the head acupoint of the second metacarpal bone of the patient, the metal member 121 of the first electrode 123 has a cylindrical shape, the first electrode 123 is electrically connected with a negative pole of the input terminal 112 via the output terminals of the substrate 110, the second end 1212 of the metal member 121 of each of the second electrodes 124 is S-shaped for being better fitted to a medial surface of the second metacarpal bone of the palm and being brought into better contact with an acupoint, each of the second electrodes 124 is electrically connected with a positive pole of the input terminal 112 via the respective output terminal of the substrate 110, and the number of the second electrodes 124 is set according to the number of the mounting portions, that is, the number of the second electrodes is set according to the number of acupoints of the preset prescriptive map of therapeutic acupoints. When the first electrode 123 is aligned with the head acupoint of the second metacarpal bone of the patient, the second electrodes 124 can also be aligned with acupoints corresponding thereto. Each metal member 121 is plated with a metal layer, and may be, for example, plated with gold in the present embodiment, and the plated metal layer can not only prevent oxidation, but also achieve a treatment with tangible needles; the conductive springs 1213 are also designed for the purpose that when the metal member 121 of each of the electrodes 120 is brought into contact with and fitted to the palm of the patient, each conductive spring 1213 can apply a certain pressure to the respective metal member 121, so that the metal member 121 is fitted more closely to the medial surface of the second metacarpal bone of the palm of the patient, and is brought into better contact with the respective acupoint, enabling the patient to have a better experience in use.

As shown in FIG. 7, the housing 140 comprises a panel 141 and a side wall 143, wherein the housing 140 has a shape matching the substrate 110 so that the housing 140 can cover the substrate 110, and the housing 140 is made of an insulating material such as plastic. The panel 141 of the housing 140 is provided with a plurality of through holes 142, each of the through holes 142 corresponds to one mounting portion, and the shape and size of each of the through holes 142 is matched with the shape and size of the corresponding electrode 120, each of the through holes is larger than a cross-sectional shape of the metal member 121 of the respective electrode 120, and is smaller than the size of the base 122 of the respective electrode 120, so that the metal member 121 of each electrode 120 can be exposed through the corresponding through hole 142, and the through hole assists in better fixing the electrode 120 to the substrate 110. The panel 141 may be formed by an arrangement and combination of grid squares with a side length of 1 mm, such that it is cut conveniently to expose the electrodes 120, which allows an easier machining and a more aesthetically pleasing appearance.

Second Embodiment

Figure 9:
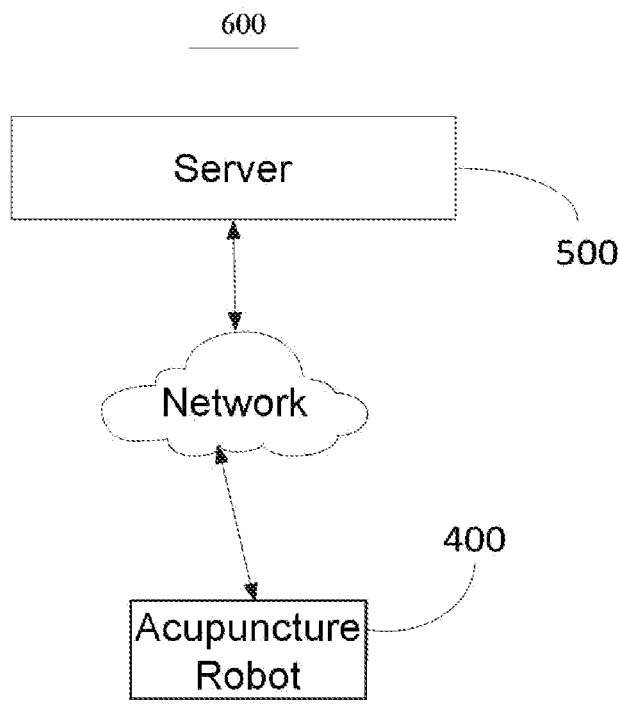
FIG. 9 shows a schematic interaction diagram of an intelligent acupuncture system according to an embodiment of the present disclosure.

Referring to FIG. 9, the present embodiment provides an intelligent acupuncture system 600, comprising the acupuncture robot 400 according to the first embodiment and a server 500, wherein the acupuncture robot 400 is in communication connection with the server 500. The server 500 stores an operation instruction, and the acupuncture robot 400 sends a request to the server 500 and acquires the operation instruction, and performs acupuncture massage treatment on a patient according to the operation instruction.

The server 500 may be set up and operated and maintained by a medical healthcare enterprise. When the patient uses the acupuncture robot 400, the patient's own disease information is sent by the acupuncture robot 400, an operation instruction for acupuncture massage for treating the disease is pre-stored in the server 500, and the acupuncture robot 400 acquires the operation instruction from the server 500, and performs acupuncture massage treatment on the patient according to the operation instruction, or instructs the patient to use the acupuncture robot 400 or performs other operations.

The acupuncture robot 400 may also send a therapeutic effect or the like to the server 500, which facilitates the follow-up treatment and management of the patient by the medical healthcare enterprise, etc.

In summary, the present disclosure provides an acupuncture robot and an intelligent acupuncture system and method, comprising an acupuncture treatment host, a palm fixing frame, and a treatment electrode, wherein the treatment electrode is tailor-made (customized) for a patient, and stores physiological feature information and disease information of the patient; the palm fixing frame is capable of fixing a palm, such that a doctor does not need to hold a hand-held treatment pen for a long time to perform acupuncture treatment, thereby improving the doctor's operational experience, and the palm fixing frame assists in the alignment of the treatment electrode with acupoints of the patient where acupuncture massage treatment is required, thereby improving the accuracy of accurately pressing the acupoints and facilitating the fixation, whereby both binding of the palm and alignment with the acupoints are satisfied, therefore the disclosure has the characteristic of a good prospect of popularization.

Additionally, the acupuncture treatment host is configured to be in communication connection with a server, and may send a therapeutic effect to the server and acquire an operation instruction from the server. The intelligent acupuncture system comprises an acupuncture robot and a server. The acupuncture robot acquires an operation instruction from the server and performs acupuncture massage on a patient according to the operation instruction, and may also send the therapeutic effect to the server. The invention of the acupuncture robot and the intelligent acupuncture system and method enables medical personnel to grasp the treatment condition of a patient in time, and remotely instruct the patient to operate and use the acupuncture robot to provide better service to the patient.

Figure 10:
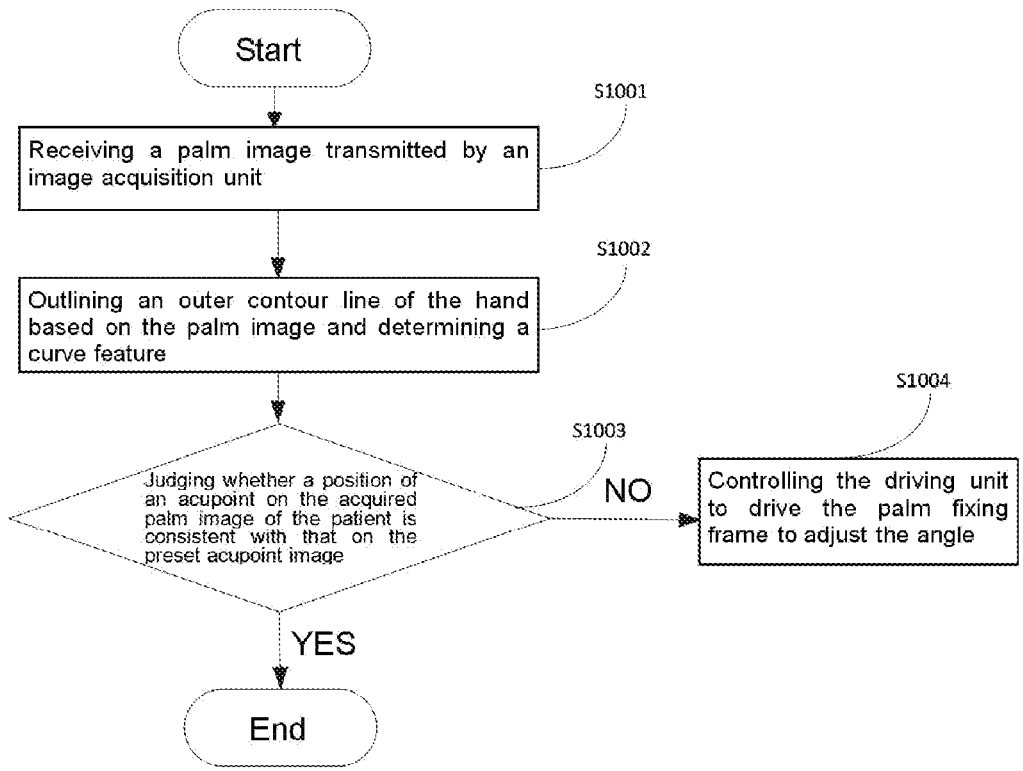
FIG. 10 shows a flowchart of an intelligent acupuncture method according to an embodiment of the present disclosure.

Referring to FIG. 10, the present disclosure further provides an intelligent acupuncture method applicable to the acupuncture robot or the intelligent acupuncture system described in the foregoing embodiment. It should be noted that the intelligent acupuncture method according to the present embodiment has the same basic principle and brings the same technical effects as the foregoing embodiment, and for parts of the present embodiment that are not mentioned, reference can be made to corresponding contents in the foregoing embodiment for the sake of brevity of the description. The intelligent acupuncture method comprises:

step S1001: receiving a palm image transmitted by an image acquisition unit 240;

step S1002: outlining an outer contour line of a hand based on the palm image and determining a curve feature;

step S1003: judging whether the position of head acupoint in the acquired palm image is consistent with the position of a red indicating line for head acupoint of a pre-stored acupoint image; wherein ending the process if the judgment result is "consistent", and executing step S1004 if the judgment result is "not consistent"; and step S1004: controlling the driving unit to drive the palm fixing frame to adjust the angle until the position of the head acupoint in the palm image is consistent with the position of the red indicating line for head acupoint of the pre-stored acupoint image.

The above description is merely illustrative of preferred embodiments of the present disclosure and is not intended to limit the present disclosure. It would be understood by those skilled in the art that various modifications and variations can be made to the present disclosure. Any modifications, equivalent alternatives, improvements and so on made within the spirit and principle of the present disclosure are to be included in the scope of protection of the present disclosure.

The invention claimed is:

1. An acupuncture robot, comprising: an acupuncture treatment host, a palm fixing frame, and a treatment electrode,
    wherein the acupuncture treatment host is mounted to the palm fixing frame, and the treatment electrode is embedded in the palm fixing frame and electrically connected with the acupuncture treatment host;
    the acupuncture treatment host comprises a control unit, a communication unit, and an electrical pulse circuit, both the communication unit and the electrical pulse circuit are connected with the control unit, and the control unit is configured to receive and process data;
    the communication unit is configured to establish a communication connection between the control unit and a server to acquire an operation instruction sent by the server and send a therapeutic effect to the server;
    the electrical pulse circuit is further connected with the treatment electrode and configured to output an electrical pulse signal to the treatment electrode according to the operation instruction under a control of the control unit to perform acupuncture massage treatment on a patient, and the palm fixing frame is configured to fix a palm of the patient; and
    the treatment electrode is configured to convert the electrical pulse signal into electrical stimulation to perform the acupuncture massage treatment on the patient,
    wherein the palm fixing frame comprises a grip rod and a treatment baseplate; the grip rod comprises a grip portion and a movable portion, the movable portion comprises a first connecting portion and a second connecting portion opposite to the first connecting portion, the first connecting portion of the movable portion is rotatably connected with the treatment baseplate, and the grip portion is rotatably connected to the second connecting portion.

2. The acupuncture robot according to claim 1, wherein the communication unit is configured to acquire the operation instruction from the server according to an instruction from the control unit, the operation instruction comprises acupoints for acupuncture treatment of the patient, a duration of the acupuncture treatment of the patient, a number of times of the acupuncture treatments of the patient, and a current magnitude for the acupuncture treatment of the patient.

3. The acupuncture robot according to claim 1, wherein the treatment baseplate comprises a control plate and a treatment plate, the acupuncture treatment host is mounted to the control plate, and the treatment electrode is embedded in the treatment plate.

4. The acupuncture robot according to claim 1, wherein the treatment electrode comprises a substrate, a first electrode, a plurality of second electrodes, and a housing, the substrate is provided with a plurality of mounting portions, positions where the plurality of mounting portions are distributed on the substrate are matched with a distribution of acupoints of a preset prescriptive map of therapeutic acupoints, and each of the first electrode and the plurality of second electrodes is corresponding to and mounted to one of the mounting portions.

5. The acupuncture robot according to claim 4, wherein the housing has a shape and size matching the substrate, the housing is provided with a plurality of through holes, a position of each of the through holes is corresponding to the position of the respective mounting portion, and the treatment electrode is exposed through the through holes.

6. The acupuncture robot according to claim 4, wherein the treatment electrode further comprises an electronic tag, and the electronic tag is mounted to the substrate and configured to store treatment information of the patient and physiological feature information of the patient.

7. The acupuncture robot according to claim 6, wherein the acupuncture treatment host further comprises an identification unit, the identification unit is electrically connected with the control unit, and the identification unit is configured to read the physiological feature information and the treatment information which are stored in the electronic tag.

8. The acupuncture robot according to claim 4, wherein each of the first electrode and the plurality of second electrodes comprises a metal member, a base, and a conductive spring, the metal member comprises a first end and a second end, the first end extends over the base and is fixedly connected with the base, and the conductive spring is disposed at the first end.

9. The acupuncture robot according to claim 1, wherein the acupuncture treatment host further comprises a button unit and a display unit, the button unit and the display unit are electrically connected with the control unit, respectively, the button unit is configured to obtain an operation instruction inputted by a user, and the control unit is configured to process the operation instruction and transmit the operation instruction to the display unit for display.

10. The acupuncture robot according to claim 1, wherein the acupuncture robot further comprises an image acquisition unit and a driving unit, both the image acquisition unit and the driving unit are electrically connected with the control unit, the image acquisition unit is configured to acquire a palm image of a hand of the patient and transmit the palm image to the control unit, and the control unit is configured to outline an outer contour line of the hand based on the palm image and determine a curve feature, judge whether a position of head acupoint in the palm image is consistent with a position of a red indicating line for head acupoint of a pre-stored acupoint image in a server, and control the driving unit to drive the palm fixing frame to adjust an angle between the grip portion and the movable portion if the position of the head acupoint in the palm image is not consistent with the position of the red indicating line for head acupoint of the pre-stored acupoint image.

11. The acupuncture robot according to claim 1, wherein the acupuncture robot further comprises an image acquisition unit and a speaker, the image acquisition unit and the speaker are electrically connected with the control unit, respectively, the image acquisition unit is configured to acquire a palm image of a hand of the patient and transmit the palm image to the control unit, and the control unit is configured to outline an outer contour line of the hand based on the palm image and determine a curve feature, judge whether a position of head acupoint in the palm image is consistent with a position of a red indicating line for head acupoint of a pre-stored acupoint image in a server, and generate a voice prompt based on a judgment result, and transmit the voice prompt to the speaker for playing.

12. The acupuncture robot according to claim 1, wherein the acupuncture treatment host further comprises a power source, the power source is electrically connected with the control unit, the communication unit, and the electrical pulse circuit, respectively, and configured to supply power to the control unit, the communication unit, the electrical pulse circuit, and the treatment electrode.

13. The acupuncture robot according to claim 12, wherein the power source comprises a storage battery, an overvoltage and overcurrent protection circuit, and a voltage stabilizing circuit, and the storage battery, the overcurrent and overvoltage protection circuit, the voltage stabilizing circuit, and the control unit are electrically connected sequentially.

14. The acupuncture robot according to claim 1, wherein the communication unit is a wireless communication unit.

15. An intelligent acupuncture system, comprising: a server and the acupuncture robot according to claim 1, wherein the acupuncture robot is in communication with the server, an operation instruction is stored in the server, and the acupuncture robot sends a request to the server and acquires the operation instruction, and performs acupuncture massage treatment on the patient according to the operation instruction.

* * * * *